United States Patent
Focht et al.

(10) Patent No.: US 9,675,530 B2
(45) Date of Patent: *Jun. 13, 2017

(54) STRIPED LIQUID PERSONAL CLEANSING COMPOSITIONS CONTAINING A CLEANSING PHASE AND A SEPERATE BENEFIT PHASE

(75) Inventors: Heather Lynn Focht, Hamilton, OH (US); Christopher Dean Putman, West Chester, OH (US); Cheyne Pohlman Thomas, Independence, KY (US); Karl Shiqing Wei, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 788 days.

This patent is subject to a terminal disclaimer.

(21) Appl. No.: 10/665,670

(22) Filed: Sep. 18, 2003

(65) Prior Publication Data
US 2004/0057920 A1    Mar. 25, 2004

Related U.S. Application Data

(60) Provisional application No. 60/412,429, filed on Sep. 20, 2002, provisional application No. 60/423,572, filed on Nov. 4, 2002.

(51) Int. Cl.
| | | |
|---|---|---|
| *A61K 8/02* | (2006.01) | |
| *A61Q 19/10* | (2006.01) | |
| *A61K 8/44* | (2006.01) | |
| *A61K 8/46* | (2006.01) | |
| *A61K 8/92* | (2006.01) | |

(52) U.S. Cl.
CPC .............. *A61K 8/0237* (2013.01); *A61K 8/02* (2013.01); *A61K 8/442* (2013.01); *A61K 8/463* (2013.01); *A61K 8/92* (2013.01); *A61Q 19/10* (2013.01); *A61K 2800/59* (2013.01)

(58) Field of Classification Search
None
See application file for complete search history.

(56) References Cited

U.S. PATENT DOCUMENTS

| | | |
|---|---|---|
| 2,020,454 A | 11/1935 | Bisbee et al. |
| 2,658,072 A | 11/1953 | Kosmin |
| 2,986,271 A | 5/1961 | Forrer |
| 3,455,440 A | 7/1969 | West |
| 3,479,429 A | 11/1969 | Morshauser et al. |
| 3,533,955 A | 10/1970 | Pader et al. |
| 3,542,256 A | 11/1970 | Waterman |
| 3,618,757 A | 11/1971 | Funkhouser |
| 3,800,998 A | 4/1974 | Gask |
| 3,850,365 A | 11/1974 | Dietrich |
| 3,852,475 A | 12/1974 | Tarangul |
| 3,899,076 A | 8/1975 | Florian |
| 3,929,678 A | 12/1975 | Laughlin et al. |
| 3,937,811 A | 2/1976 | Papantoniou et al. |
| 3,951,679 A | 4/1976 | Bernhard et al. |
| 3,980,767 A | 9/1976 | Chown et al. |
| 4,159,028 A | 6/1979 | Barker et al. |
| 4,263,363 A | 4/1981 | Buck et al. |
| 4,335,103 A | 6/1982 | Barker et al. |
| 4,379,753 A | 4/1983 | Bolich, Jr. |
| 4,425,322 A | 1/1984 | Harvey et al. |
| 4,518,578 A | 5/1985 | Hayes et al. |
| D292,879 S | 11/1987 | Smith |
| 4,966,205 A | 10/1990 | Tanaka |
| 4,980,155 A | 12/1990 | Shah et al. |
| 5,002,680 A | 3/1991 | Schmidt et al. |
| 5,059,414 A | 10/1991 | Dallal et al. |
| 5,223,315 A | 6/1993 | Katsura et al. |
| 5,228,912 A | 7/1993 | Herget et al. |
| 5,304,334 A | 4/1994 | Lahanas et al. |
| 5,393,450 A | 2/1995 | Shana'a et al. |
| 5,455,035 A | 10/1995 | Guerrero et al. |
| 5,487,168 A | 1/1996 | Geiner et al. |
| 5,540,853 A | 7/1996 | Trinh et al. |
| 5,556,628 A * | 9/1996 | Derian et al. ................. 424/401 |
| 5,578,299 A | 11/1996 | Starch |
| 5,612,307 A | 3/1997 | Chambers et al. |
| 5,632,420 A | 5/1997 | Lohrman et al. |
| 5,661,189 A | 8/1997 | Grievson et al. |
| 5,687,779 A | 11/1997 | Andersson et al. |
| 5,716,920 A * | 2/1998 | Glenn et al. ................. 510/159 |
| 5,851,978 A | 12/1998 | Shana'a |
| 5,853,707 A * | 12/1998 | Wells et al. ................ 424/70.12 |
| 5,873,494 A | 2/1999 | Dallas, Jr. |
| 5,914,117 A | 6/1999 | Lavaud |
| 5,925,603 A | 7/1999 | D'Angelo |
| 5,929,019 A | 7/1999 | Puvvada et al. |
| 5,947,335 A | 9/1999 | Milio et al. |
| 5,952,286 A | 9/1999 | Puvvada et al. |
| 5,954,213 A | 9/1999 | Gerhart et al. |

(Continued)

FOREIGN PATENT DOCUMENTS

| | | |
|---|---|---|
| CA | 2246316 | 6/1998 |
| DE | 19650952 A | 6/1998 |

(Continued)

OTHER PUBLICATIONS

XP 002332778 "Dove All Day Moisturizing Body Wash" Online URL: http://www.ewg.org/reprots/skindeep/productinfo.php?prod_id=901910.
XP002332779 "Olay Daily Renewal Moisturizing Body Wash" Online URL: http://householdprdoucts.nlm.nih.gov/cgi-bin/household.brands?tbl=brands&id=16003084.
U.S. Appl. No. 10/050,494, filed Jan. 16, 2002, Wei et al.
U.S. Appl. No. 10/358,803, filed Feb. 5, 2003, Putnam et al.

(Continued)

*Primary Examiner* — Lakshmi Channavajjala

(57) ABSTRACT

Personal cleansing compositions comprise (A) a cleansing phase containing a surfactant and water; and (B) a separate benefit phase containing a hydrophobic material; wherein the cleansing and benefit phases are packaged together and are in physical contact. The two phases are packaged in physical contact and remain separate and stable at ambient conditions for at least 180 days. These compositions and corresponding methods provide improved cosmetics, skin feel, and/or skin benefit efficacy.

21 Claims, No Drawings

(56) References Cited

U.S. PATENT DOCUMENTS

| | | | |
|---|---|---|---|
| 5,965,500 A | 10/1999 | Puvvada | |
| 5,965,501 A | 10/1999 | Rattinger et al. | |
| 5,972,361 A | 10/1999 | Fowler et al. | |
| D426,158 S | 6/2000 | Flurer et al. | |
| 6,174,845 B1 | 1/2001 | Rattinger et al. | |
| 6,176,391 B1 | 1/2001 | Rehkemper et al. | |
| 6,176,395 B1 | 1/2001 | Abbott et al. | |
| 6,190,648 B1 | 2/2001 | Kouzu et al. | |
| 6,194,364 B1 | 2/2001 | Glenn, Jr. | |
| D438,460 S | 3/2001 | Hammond | |
| D439,165 S | 3/2001 | Erckelbout et al. | |
| 6,213,166 B1 | 4/2001 | Thibiant et al. | |
| D441,645 S | 5/2001 | Longhurst | |
| 6,232,496 B1 | 5/2001 | Carr et al. | |
| 6,245,323 B1 | 6/2001 | Christie et al. | |
| 6,245,344 B1 | 6/2001 | Thibiant et al. | |
| 6,268,322 B1 | 7/2001 | St. Lewis et al. | |
| 6,306,806 B1 | 10/2001 | St. Lewis et al. | |
| 6,335,312 B1 | 1/2002 | Coffindaffer et al. | |
| 6,340,723 B1 | 1/2002 | Nitta et al. | |
| D455,655 S | 4/2002 | Bunce | |
| 6,367,519 B2 | 4/2002 | Thibiant et al. | |
| 6,383,999 B1 | 5/2002 | Coyle et al. | |
| 6,385,992 B1 | 5/2002 | Flore, Jr. | |
| 6,394,323 B2 | 5/2002 | McClean et al. | |
| 6,419,783 B1 | 7/2002 | Rainey et al. | |
| 6,426,326 B1 | 7/2002 | Mitra et al. | |
| 6,429,177 B1 | 8/2002 | Salmon et al. | |
| 6,495,496 B2 * | 12/2002 | Gutierrez et al. | 508/561 |
| 6,495,498 B2 | 12/2002 | Niemiec et al. | |
| 6,506,391 B1 | 1/2003 | Biatry | |
| 6,517,939 B1 | 2/2003 | Moini et al. | |
| 6,521,216 B1 | 2/2003 | Glendorf et al. | |
| 6,534,456 B2 * | 3/2003 | Hayward et al. | 510/130 |
| 6,534,457 B2 * | 3/2003 | Mitra | 510/130 |
| 6,547,063 B1 | 4/2003 | Zaveri et al. | |
| 6,555,509 B2 | 4/2003 | Abbas et al. | |
| 6,564,978 B1 | 5/2003 | Safian et al. | |
| 6,574,985 B2 | 6/2003 | Fiore, Jr. | |
| 6,589,509 B2 | 7/2003 | Keller et al. | |
| 6,652,134 B2 | 11/2003 | Lloyd | |
| 6,663,855 B2 | 12/2003 | Frechet et al. | |
| 6,673,371 B2 | 1/2004 | Brown et al. | |
| 6,673,755 B2 * | 1/2004 | Wei et al. | 510/130 |
| D486,395 S | 2/2004 | Lovell et al. | |
| D486,398 S | 2/2004 | Lovell et al. | |
| 6,691,394 B1 | 2/2004 | McClean | |
| 6,695,510 B1 | 2/2004 | Look et al. | |
| 6,782,307 B2 | 8/2004 | Wilmott et al. | |
| 6,919,303 B2 | 7/2005 | Pham et al. | |
| 6,924,256 B2 | 8/2005 | Massaro et al. | |
| 7,143,893 B2 | 12/2006 | Kelly | |
| 7,144,542 B2 | 12/2006 | Holzer et al. | |
| 7,229,486 B2 | 6/2007 | Wiersema et al. | |
| 7,273,837 B2 | 9/2007 | Boutique et al. | |
| 7,511,003 B2 | 3/2009 | Focht et al. | |
| 7,524,807 B2 | 4/2009 | Clapp et al. | |
| 7,666,825 B2 | 2/2010 | Wagner et al. | |
| 8,084,408 B2 * | 12/2011 | Wei et al. | 510/130 |
| 8,105,996 B2 * | 1/2012 | Wei et al. | 510/130 |
| 8,124,573 B2 * | 2/2012 | Focht et al. | 510/130 |
| 8,158,566 B2 * | 4/2012 | Wei | 510/130 |
| 8,314,054 B2 * | 11/2012 | Wagner et al. | 510/130 |
| 2001/0036467 A1 | 11/2001 | Thibiant et al. | |
| 2002/0004468 A1 | 1/2002 | Hodge et al. | |
| 2002/0010110 A1 | 1/2002 | Hayward et al. | |
| 2002/0022040 A1 | 2/2002 | Robinson et al. | |
| 2003/0003069 A1 | 1/2003 | Carson et al. | |
| 2003/0180246 A1 | 9/2003 | Frantz et al. | |
| 2004/0048757 A1 | 3/2004 | Zhang et al. | |
| 2004/0048758 A1 | 3/2004 | Zhang et al. | |
| 2004/0057920 A1 | 3/2004 | Focht et al. | |
| 2004/0091445 A1 | 5/2004 | Dykstra et al. | |
| 2004/0101492 A1 * | 5/2004 | Dolan | A61K 8/0237 424/49 |
| 2004/0105827 A1 | 6/2004 | Grimm et al. | |
| 2004/0146475 A1 | 7/2004 | Peffly et al. | |
| 2004/0158940 A1 | 8/2004 | Wells et al. | |
| 2004/0180020 A1 | 9/2004 | Manelski et al. | |
| 2004/0219119 A1 | 11/2004 | Wei et al. | |
| 2004/0223939 A1 | 11/2004 | Clausen et al. | |
| 2004/0223991 A1 | 11/2004 | Wei et al. | |
| 2004/0223992 A1 | 11/2004 | Clapp et al. | |
| 2004/0232023 A1 | 11/2004 | Bansal et al. | |
| 2004/0235693 A1 | 11/2004 | Wei et al. | |
| 2004/0242706 A1 | 12/2004 | Wiersema et al. | |
| 2004/0248748 A1 | 12/2004 | Wei et al. | |
| 2004/0248749 A1 | 12/2004 | Mitra et al. | |
| 2005/0003975 A1 | 1/2005 | Browne et al. | |
| 2005/0020468 A1 | 1/2005 | Frantz et al. | |
| 2005/0100570 A1 | 5/2005 | Wei et al. | |
| 2005/0139574 A1 | 6/2005 | Simone et al. | |
| 2005/0143269 A1 | 6/2005 | Wei et al. | |
| 2005/0192187 A1 | 9/2005 | Wagner et al. | |
| 2005/0192188 A1 | 9/2005 | Wagner et al. | |
| 2005/0238680 A1 | 10/2005 | Stella et al. | |
| 2005/0249758 A1 | 11/2005 | Di Puccio Pagano | |
| 2005/0269372 A1 | 12/2005 | Smith | |
| 2005/0276768 A1 | 12/2005 | Wei et al. | |
| 2006/0002880 A1 | 1/2006 | Peffly et al. | |
| 2006/0008438 A1 | 1/2006 | Velarde et al. | |
| 2006/0079419 A1 | 4/2006 | Wagner et al. | |
| 2006/0079420 A1 | 4/2006 | Wagner et al. | |
| 2006/0094628 A1 | 5/2006 | Wei et al. | |
| 2006/0210505 A1 | 9/2006 | Clapp et al. | |
| 2006/0276357 A1 | 12/2006 | Smith, III et al. | |
| 2007/0141001 A1 | 6/2007 | Clapp et al. | |
| 2007/0187274 A1 | 8/2007 | Dalea et al. | |
| 2007/0248562 A1 | 10/2007 | Berry et al. | |
| 2007/0280976 A1 | 12/2007 | Taylor et al. | |
| 2010/0209374 A1 | 8/2010 | Wei et al. | |

FOREIGN PATENT DOCUMENTS

| | | |
|---|---|---|
| DE | 198 54 086 A | 5/2000 |
| EP | 0 078138 A2 | 5/1983 |
| EP | 0 331617 B | 4/1992 |
| EP | 882 442 A1 * | 12/1998 |
| EP | 1 108421 A2 | 6/2001 |
| EP | 1 005849 B1 | 9/2001 |
| EP | 1 064918 B1 | 9/2002 |
| EP | 0 907345 B1 | 5/2003 |
| GB | 1277324 A | 6/1972 |
| JP | 2000229817 A | 8/2000 |
| JP | 2002-128639 A | 5/2002 |
| JP | 2002-138010 A | 5/2002 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 98/33477 | 8/1998 |
| WO | WO 99/38489 A1 | 8/1999 |
| WO | WO 99/38491 A1 | 8/1999 |
| WO | WO 00/75240 A1 | 12/2000 |
| WO | WO 01/01931 A3 | 1/2001 |
| WO | WO 01/70193 A2 | 9/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |
| WO | WO 2005/067875 A1 | 7/2005 |

OTHER PUBLICATIONS

"Solubility, Effects in Product, Package, Penetration and Preservation", C.D. Vaughan, Cosmetics and Toiletries, vol. 103, Oct. 1988, pp. 47-69.

XP 002332778 "Dove All Day Moisturizing Body Wash" Online URL: http://www.ewg.org/reports/skindeep2/report.

(56) References Cited

OTHER PUBLICATIONS php?type=PRODUCT&id=8801874, accessed Feb. 8, 2006 (6 pages).
C.D. Vaughan, "Solubility, Effects in Product, in Package, Penetration and Preservation," Cosmetic and Toiletries, vol. 103, Oct. 1988.
Crank, Mathematics of Diffusion, $2^{nd}$ Edition, nma 1975, p. 63.
CTFA International Cosmetic Ingredient Dictionary, Fourth Edition, Aug. 12, 1991, pp. 12 and 80.
Household Products Database, Brand Information, "Olay Daily Renewal Moisturizing Body Wash, Calming," [Online] URL: http://householdproducts.nlm.nih.gov/cgi-bin/household/brands?tbl=brands&id=16003084, accessed Feb. 8, 2006 (2 pages).
Milton, Introduction to Probability and Statistics, $4^{th}$ Edition (Section 9.2: Testing Hypotheses on a Proportion), pp. 129-131, accessed Jun. 9, 2008.
J. Caelles et al., "Anionic and Cationic Compounds in Mixed Systems,"Cosmetics & Toiletries, vol. 106, Apr. 1991. pp. 49-54.
C.J. van Oss, "Coacervation, Complex-Coacervation and Flocculation," J. Dispersion Science and Technology, vol. 9 (5, 6), 1988-89, p. 561-573.
D.J. Burgess, "Practical Analysis of Complex Coacervate Systems," J. of Colloid Anti Interface Science, vol. 140, No. 1, Nov. 1990, pp. 227-238.
KOBO Brochure, "Treated Pigments" (May 2000).

\* cited by examiner

STRIPED LIQUID PERSONAL CLEANSING COMPOSITIONS CONTAINING A CLEANSING PHASE AND A SEPERATE BENEFIT PHASE

CROSS REFERENCE TO RELATED APPLICATIONS

This application claims the benefit of U.S. Provisional Application No. 60/412,429, filed Sep. 20, 2002 and U.S. Provisional Application No. 60/423,572, filed Nov. 4, 2002.

FIELD OF THE INVENTION

The present invention relates to striped liquid personal cleansing compositions comprising a cleansing phase and a separate benefit phase wherein the two phases are packaged in physical contact while remaining stable for long periods of time.

BACKGROUND OF THE INVENTION

Personal cleansing compositions that attempt to provide skin-conditioning benefits are known. Many of these compositions are aqueous systems comprising an emulsified conditioning oil or other similar materials in combination with a lathering surfactant. Although these products provide both conditioning and cleansing benefits, it is often difficult to formulate a product that deposits sufficient amount of skin conditioning agents on skin during use. In order to combat emulsification of the skin conditioning agents by the cleansing surfactant, large amounts of the skin conditioning agent are added to the compositions. However, this introduces another problem associated with these dual cleansing and conditioning products. Raising the level of skin conditioning agent in order to achieve increased deposition negatively affects product lather performance and stability.

One attempt at providing conditioning and cleansing benefits from a personal cleansing product while maintaining stability has been the use of dual-chamber packaging. These packages comprise separate cleansing compositions and conditioning compositions, and allow for the co-dispensing of the two in a single or dual stream. The separate conditioning and cleansing compositions thus remain physically separate and stable during prolonged storage and just prior to application, but then mix during or after dispensing to provide conditioning and cleansing benefits from a physically stable system. Although such dual-chamber delivery systems provide improved conditioning benefits over the use of conventional systems, it is often difficult to achieve consistent and uniform performance because of the uneven dispensing ratio between the cleansing phase and the conditioning phase from these dual-chamber packages. Additionally, these packaging systems add considerable cost to the finished product.

Accordingly, the need still remains for a personal cleansing composition that provides both cleansing and improved skin conditioning benefits. The need also remains for a personal cleansing composition comprising two phases in physical contact that remain stable for long periods of time.

It is therefore an object of the present invention to provide a striped liquid personal cleansing composition comprising cleansing and benefit phases that are packaged in physical contact while remaining stable, wherein the compositions provide improved deposition of conditioning agents on skin.

It has now been found that a striped liquid personal cleansing composition containing both cleansing and benefit phases that are packaged in physical contact while remaining stable, can be formulated to provide improved cosmetics and skin feel during and after application while also providing excellent skin conditioning and cleansing benefits. It has been found that such a composition can be formulated with sufficiently high levels of benefit agents without compromising product lather performance and stability. Superior lather performance can be demonstrated via the lather volume method described herein.

It has also been found that striped personal cleansing compositions can be formulated with selected skin active agents that provide improved chronic skin benefits to the desired area of the skin. These compositions comprise a cleansing phase containing a cleansing surfactant and at least one additional separate phase containing a skin active agent, wherein the cleansing and active phases are packaged in physical contact while remaining stable for long periods of time.

SUMMARY OF THE INVENTION

The present invention is directed to a striped personal cleansing composition comprising first stripe comprising a cleansing phase comprising a surfactant, water, and optional conventional personal cleansing ingredients and at least one additional stripe comprising a separate benefit phase containing at least about 20% by weight of a hydrophobic material having a Vaughan Solubility Parameter of from about 5 to about 15, wherein the benefit phase has a Consistency value of from about 1 to about 10,000 poise.

The present invention further relates to a striped liquid personal cleansing composition comprising:
a) a cleansing phase comprising from about 1% to about 50% by weight of the cleansing phase of a surfactant selected from the group consisting of anionic surfactant, non-ionic surfactant, zwitterionic surfactant, cationic surfactant, soap and mixtures thereof;
wherein the cleansing phase is non-Newtonian shear thinning, and has a viscosity of equal to or greater than about 3,000 cps and a yield value of at least about 0.1 Pa; and
b) a benefit phase comprising from about 20% to about 100% by weight of the benefit phase of a hydrophobic material selected from the group consisting of lipids, hydrocarbons, fats, oils, hydrophobic plant extracts, fatty acids, essential oils, silicone oils, and mixtures thereof;
wherein the hydrophobic material has a Vaughan Solubility Parameter of about 5 to about 15 and further wherein the weight ratio between the cleansing phase and the benefit phase is from about 1:9 to about 99:1 and the cleansing phase and benefit phase are in physical contact in the same package and remain stable in ambient conditions for at least about 180 days; and wherein the cleansing phase and benefit phase are present as stripes wherein the stripe size is at least about 0.1 mm in width and at least about 1 mm in length.

The present invention further relates to a striped personal cleansing composition comprising a cleansing phase and benefit phase wherein at least one phase contains a colorant, wherein both phases are packed in a single package such that the two phases form a pattern.

The present invention is also directed to a method of cleansing and moisturizing the skin by applying to the skin a composition as described above. These compositions provide improved deposition of skin benefit agents on skin during application.

DETAILED DESCRIPTION

The striped personal cleansing compositions and methods of the present invention comprise personal cleansing compositions comprising a first stripe comprising a cleansing phase and at least one additional stripe comprising a separate benefit phase. These and other essential limitations of the compositions and methods of the present invention, as well as many of the optional ingredients suitable for use herein, are described in detail hereinafter.

The term "anhydrous" as used herein, unless otherwise specified, refers to those compositions or materials containing less than about 10%, more preferably less than about 5%, even more preferably less than about 3%, even more preferably zero percent, by weight of water.

The term "ambient conditions" as used herein, unless otherwise specified, refers to surrounding conditions at one (1) atmosphere of pressure, 50% relative humidity, and 25° C.

The term "stable" as used herein, unless otherwise specified, refers to compositions that maintain at least two "separate" phases in physical contact at ambient conditions for a period of at least about 180 days. By "separate" is meant that there is substantially no mixing, observable to the naked eye, prior to dispensing of the composition.

The term "personal cleansing composition" as used herein, unless otherwise specified, refers to the compositions of the present invention, wherein the compositions are intended to include only those compositions for topical application to the skin or hair, and specifically excludes those compositions that are directed primarily to other applications such as hard surface cleansing, fabric or laundry cleansing, and similar other applications not intended primarily for topical application to the hair or skin.

The Vaughan Solubility Parameter (VSP) as used herein is a parameter used to define the solubility of hydrophobic materials. Vaughan Solubility parameters are well known in the various chemical and formulation arts and typically have a range of from 5 to 25.

The term "Consistency value" or "k" as used herein is a measure of lipid viscosity and is used in combination with Shear Index, to define viscosity for materials whose viscosity is a function of shear. The measurements are made at 35° C. and the units are poise (equal to 100 cps).

The term "Shear Index" or "n" as used herein is a measure of lipid viscosity and is used in combination with Consistency value, to define viscosity for materials whose viscosity is a function of shear. The measurements are made at 35° C. and the units are dimensionless.

The phrase "substantially free of" as used herein, unless otherwise specified means that the composition comprises less than about 5%, preferably less than about 3%, more preferably less than about 1% and most preferably less than about 0.1% of the stated ingredient.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

All cited references are incorporated herein by reference in their entireties. Citation of any reference is not an admission regarding any determination as to its availability as prior art to the claimed invention.

The personal cleansing compositions and methods of the present invention can comprise, consist of, or consist essentially of, the essential elements and limitations of the invention described herein, as well as any additional or optional ingredients, components, or limitations described herein or otherwise useful in personal cleansing compositions intended for topical application to the hair or skin.

Product Form

The personal cleansing compositions of the present invention can be in the form of liquid, semi-liquid, cream, lotion or gel compositions intended for topical application to skin. These compositions contain a cleansing phase and a benefit phase, both of which are described in greater detail hereinafter.

All of the product forms contemplated for purposes of defining the compositions and methods of the present invention are rinse-off formulations, by which is meant the product is applied topically to the skin or hair and then subsequently (i.e., within minutes) rinsed away with water, or otherwise wiped off using a substrate or other suitable removal means.

Cleansing Phase

The personal cleansing compositions of the present invention comprise an aqueous cleansing phase that contains a surfactant suitable for application to the skin or hair. Suitable surfactants for use herein include any known or otherwise effective cleansing surfactant suitable for application to the skin, and which is otherwise compatible with the other essential ingredients in the aqueous cleansing phase of the compositions. These cleansing surfactants include anionic, nonionic, cationic, zwitterionic or amphoteric surfactants, or combinations thereof. The cleansing surfactant phase in the present invention exhibits Non-Newtonian shear thinning behavior. The surfactant phase has a viscosity of equal to or greater than 3,000 cps and a yield value of at least 0.1 Pa.

The aqueous cleansing phase of the personal care compositions preferably comprises a cleansing surfactant at concentrations ranging from about 1% to about 50%, more preferably from about 4% to about 30%, even more preferably from about 5% to about 25%, by weight of the aqueous cleansing phase. The preferred pH range of the cleansing phase is from about 5 to about 8.

Anionic surfactants suitable for use in the cleansing phase include alkyl and alkyl ether sulfates. These materials have the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohols having from about 8 to about 24 carbon atoms. Preferably, R has from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, preferably from about 3 to about 5, and more preferably with about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the cleansing phase are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1—SO_3-M]$, wherein $R^1$ is chosen from the group consisting of a straight or branched chain, saturated aliphatic hydrocarbon radical having from about 8 to about 24, preferably about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Other suitable surfactants are described in *McCutcheon's, Emulsifiers and Detergents,* 1989 *Annual,* published by M. C. Publishing Co., and in U.S. Pat. No. 3,929,678.

Preferred anionic surfactants for use in the cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium trideceth sulfate, for example, are preferred in some embodiments. Mixtures of anionic surfactants may be used in some embodiments.

Additional surfactant from the classes of amphoteric, zwitterionic surfactant, cationic surfactant, and/or nonionic surfactant may be incorporated in the cleansing phase compositions.

Amphoteric surfactants suitable for use in the cleansing phase include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

Zwitterionic surfactants suitable for use in the cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

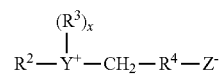

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use in the cleansing phase include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH $(CH_2)_3$ radical is attached to the nitrogen atom of the betaine are also useful in this invention.

Amphoacetates and diamphoacetates may also be used.

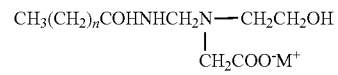

Amphoacetate

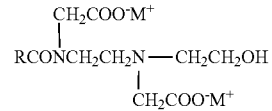

Diamphoacetate

Amphoacetates and diamphoacetates conform to the formulas (above) where R is an aliphatic group of 8 to 18 carbon atoms. M is a cation such as sodium, potassium, ammonium, or substituted ammonium. Sodium lauroamphoacetate, sodium cocoamphoactetate, disodium lauroamphoacetate, and disodium cocodiamphoacetate are preferred in some embodiments.

Cationic surfactants can also be used in the cleansing phase, but are generally less preferred, and preferably represent less than about 5% by weight of the compositions.

Suitable nonionic surfactants for use in the aqueous cleansing phase include condensation products of alkylene oxide groups (hydrophilic in nature) with an organic hydrophobic compound, which may be aliphatic or alkyl aromatic in nature.

Viscosity of Cleansing Phase Composition

The Wells-Brookfield Cone/Plate Model DV-II+ can be used to determine the viscosity of the personal cleansing composition described herein. The determination is performed at 25° C. with 2.4 cm 3° cone measuring system with a gap of 0.013 mm between the two small pins on the respective cone and plate. The measurement is performed by injecting 0.5 ml. of the sample to be analyzed between the cone and the plate and toting the cone at a set speed of 1 rpm. The resistance to rotation of the cone produces a torque that is proportional to the shear stress of the liquid sample. The amount of torque is read and computed by the viscometer into absolute centipoises units (mPa*s) based on geometric constant of the cone, the rate of rotation, and the stress related torque.

Yield Point of Cleansing Phase Composition

The Carrimed CSL 100 Controlled Stress Rheometer can be used to determine the yield point of the personal cleansing composition described herein. For purposes herein, the yield point is the amount of stress required to produce a strain of 1% on the personal cleansing composition. The determination is performed at 25° C. with the 4 cm 2° cone measuring system set with a 51 micron gap. The determination is performed via the programmed application of shear stress (typically from about 0.06 dynes/sq. centimeter to about 500 dynes/sq. centimeter) over time. This amount of stress results in a deformation of the sample. A shear stress versus strain curve can be created. From this curve, the yield point of the personal cleansing composition can be calculated. Multiple liquid phase compositions as disclosed herein have values greater than 0.1 Pascal.

Optional Ingredients for use in the Cleansing Phase

Other suitable optional ingredients in the cleansing phase are one or more humectants and solutes. A variety of humectants and solutes can be employed and can be present at a level of from about 0.1% to about 50%, preferably from about 0.5% to about 35%, and more preferably from about 2% to about 20% of a non-volatile, organic material having a solubility of a least 5 parts in 10 parts water. A preferred water soluble, organic material is selected from the group consisting of a polyol of the structure:

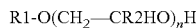

where R1=H, C1-C4 alkyl; R2=H, CH$_3$ and n=1-200; C2-C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D,L-forms); pyrrolidone carboxylic acid; hyaluronic acid; lactamide monoethanolamine; acetamide monoethanolamine; urea; and ethanol amines of the general structure (HOCH$_2$CH$_2$)$_x$NH$_y$, where x=1-3; y=0-2, and x+y=3, and mixtures thereof. The most preferred polyols are selected from the group consisting of glycerine, polyoxypropylene(1) glycerol and polyoxypropylene(3) glycerol, sorbitol, butylene glycol, propylene glycol, sucrose, urea and triethanol amine.

Nonionic polyethylene/polypropylene glycol polymers are preferably used as skin conditioning agents. Polymers useful herein that are especially preferred are PEG-2M wherein x equals 2 and n has an average value of about 2,000 (PEG 2-M is also known as Polyox WSR® N-10 from Union Carbide and as PEG-2,000); PEG-5M wherein x equals 2 and n has an average value of about 5,000 (PEG 5-M is also known as Polyox WSR® 35 and Polyox WSR® N-80, both from Union Carbide and as PEG-5,000 and Polyethylene Glycol 200,000); PEG-7M wherein x equals 2 and n has an average value of about 7,000 (PEG 7-M is also known as Polyox WSR® (N-750 from Union Carbide); PEG-9M wherein x equals 2 and n has an average value of about 9,000 (PEG 9-M is also known as Polyox WSR® N-3333 from Union Carbide); PEG-14 M wherein x equals 2 and n has an average value of about 14,000 (PEG 14-M is also known as Polyox WSR-205 and Polyox WSR® N-3000 both from Union Carbide); and PEG-90M wherein x equals 2 and n has an average value of about 90,000 (PEG-90M is also known as Polyox WSR®-301 from Union Carbide.)

Other non limiting examples of these optional ingredients include vitamins and derivatives thereof (e.g., ascorbic acid, vitamin E, tocopheryl acetate, and the like); sunscreens; thickening agents (e.g., polyol alkoxy ester, available as Crothix from Croda); preservatives for maintaining the anti microbial integrity of the cleansing compositions; anti-acne medicaments (resorcinol, salicylic acid, and the like); anti-oxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol).

In an additional embodiment of the present invention the surfactant compositions for use in the cleansing phase exhibit Non-Newtonian shear thinning behavior (herein referred to as free flowing compositions). These surfactant compositions comprise water, at least one anionic surfactant, an electrolyte and at least one alkanolamide.

The alkanolamide if present has the general structure of:

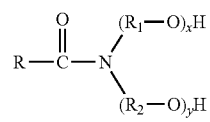

wherein R is C$_8$ to C$_{24}$ or preferably in some embodiments C$_8$ to C$_{22}$ or in other embodiments C$_8$ to C$_{18}$ saturated or unsaturated straight chain or branched aliphatic group, R$_1$ and R$_2$ are the same or different C$_2$-C$_4$ straight chain or branched aliphatic group, x=0 to 10; y=1-10 and wherein the sum of x and y is less than or equal to 10.

The alkanolamide preferably has a C$_8$ to C$_{24}$ aliphatic chain and the alkanolamide may include one to two alkanol groups which may either have a hydrocarbon backbone or an alkoxy backbone. The hydrocarbon alkanol groups may be C$_2$ to C$_4$ straight chain or branched aliphatic groups. The amount of alkanolamide in the composition is about 0.1% to about 10% by weight, and in some embodiments is preferably about 2% to about 5% by weight. Some preferred alkanolamides include Cocamide MEA (Coco monethanolamide) and Cocamide MIPA (Coco monoisopropranolamide). A co-surfactant from the classes of nonionic surfactant, amphoteric and/or zwitterionic surfactant or cationic surfactant may be optionally incorporated.

The electrolyte, if used, can be added per se to the composition or it can be composed of the counter-ions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium or ammonium chloride or sodium or ammonium sulfate.

The electrolyte should be present in an amount, which facilitates formation of the free flowing composition. Generally, this amount is from about 0.1% by weight to about 15% by weight, preferably from about 1% to about 6% by weight, but may be varied if required.

Without wishing to be bound by theory, it is believed that in some examples the compositions of the invention may have a lamellar structure. The compositions of the invention have free-flowing Non-Newtonian shear-thinning properties and the ability to suspend components (which are known characteristics of lamellar phase surfactant compositions).

Frequently surfactants are sold as solutions in water or other solvents which dilute them to less than 100% active surfactant, therefore the "active surfactant" means actual amount of surfactant delivered to the free flowing composition from a commercial surfactant preparation.

The total amount of all surfactants e.g. anionic surfactants, nonionic surfactants, amphoteric and/or zwitterionic surfactants, and cationic surfactants taken together, is typically about 8 to about 30% active surfactant and preferably about 10 to about 20% active surfactant. In some embodiments it is preferable that at least one of the surfactants has an aliphatic chain that has branching or unsaturation or a combination thereof.

The striped personal cleansing compositions of the present invention may additionally comprise an organic cationic deposition polymer in the cleansing phase as a deposition aid for the benefit agents described hereinafter. Concentrations of the cationic deposition polymer preferably range from about 0.025% to about 3%, more preferably from about 0.05% to about 2%, even more preferably from about 0.1% to about 1%, by weight of the cleansing phase composition.

Suitable cationic deposition polymers for use in the striped personal cleansing composition of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal cleansing composition, which pH will generally range from about pH 4 to about pH 9, preferably between about pH 5 and about pH 8.

The charge density can be controlled and adjusted in accordance with techniques well known in the art. As used herein the "charge density" of the cationic polymers is defined as the number of cationic sites per polymer gram atomic weight (molecular weight), and can be expressed in terms of meq/gram of cationic charge. In general, adjustment of the proportions of amine or quaternary ammonium moieties in the polymer, as well as pH of the personal cleansing composition in the case of the amines, will affect the charge density.

Any anionic counterions can be use in association with the cationic deposition polymers so long as the polymers remain soluble in water, in the personal cleansing composition, or in a coacervate phase of the personal cleansing composition, and so long as the counterions are physically and chemically compatible with the essential components of the personal cleansing composition or do not otherwise unduly impair product performance, stability or aesthetics. Nonlimiting examples of such counterions include halides (e.g., chlorine, fluorine, bromine, iodine), sulfate and methylsulfate.

Nonlimiting examples of cationic deposition polymers for use in the personal cleansing composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

The cationic polymers herein are either soluble in the cleansing phase, or preferably are soluble in a complex coacervate phase in the striped personal cleansing composition formed by the cationic deposition polymer and the anionic surfactant component described hereinbefore. Complex coacervates of the cationic deposition polymer can also be formed with other charged materials in the personal cleansing composition.

Coacervate formation is dependent upon a variety of criteria such as molecular weight, component concentration, and ratio of interacting ionic components, ionic strength (including, modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", Cosmetics & Toiletries, Vol. 106, April 1991, pp 49-54, C. J. van Oss, "Coacervation, Complex-Coacervation and Flocculation", J. Dispersion Science and Technology, Vol. 9 (5,6), 1988-89, pp 561-573, and D. J. Burgess, "Practical Analysis of Complex Coacervate Systems", J. of Colloid anti Interface Science, Vol. 140, No. 1, November 1990, pp 227-238, which descriptions are incorporated herein by reference.

It is believed to be particularly advantageous for the cationic deposition polymer to be present in the personal cleansing composition in a coacervate phase, or to form a coacervate phase upon application or rinsing of the cleansing composition to or from the skin. Complex coacervates are believed to more readily deposit on the skin, which results in improved deposition of the benefit materials. Thus, in general, it is preferred that the cationic deposition polymer exists in the personal cleansing composition as a coacervate phase or form a coacervate phase upon dilution. If not already a coacervate in the personal cleansing composition, the cationic deposition polymer will preferably exist in a complex coacervate form in the cleansing composition upon dilution with water.

Techniques for analysis of formation of complex coacervates are known in the art. For example, centrifugation analyses of the personal cleansing compositions, at any chosen stage of dilution, can be utilized to identify whether a coacervate phase has formed.

Benefit Phase

The separate benefit phase in the present invention is preferably anhydrous. The benefit phase comprises from about 20% to about 100%, preferably at least about 35%, most preferably at least about 50% of a hydrophobic skin benefit agent. The benefit agents suitable for use in the present invention have a Vaughan Solubility Parameter of from about 5 to about 15. The benefit agents are preferably selected among those having defined rheological properties as described hereinafter, including selected Consistency value (k) and Shear Index (n). These preferred rheological properties are especially useful in providing the personal cleansing compositions with improved deposition of benefit agents on skin.

Vaughan Solubility Parameter Value (VSP)

The hydrophobic skin benefit agent for use in the benefit phase of the composition has a Vaughan Solubility Parameter (VSP) of from about 5 to about 15 $(cal/cm^3)^{0.5}$, preferably from about 6 to less than 10 $(cal/cm^3)^{0.5}$, more preferably from about 6 to about 9 $(cal/cm^3)^{0.5}$. These solubility parameters are well known in the formulation arts, and are defined by Vaughan in *Cosmetics and Toiletries*, Vol. 103, p 47-69, October 1988.

Non-limiting examples of hydrophobic skin benefit agent having VSP values ranging from about 5 to about 15 $(cal/cm^3)^{0.5}$ include the following:

| VAUGHAN SOLUBILITY PARAMETERS* $(cal/cm^3)^{0.5}$ | |
|---|---|
| Cyclomethicone | 5.92 |
| Squalene | 6.03 |
| Petrolatum | 7.33 |
| Isopropyl Palmitate | 7.78 |
| Isopropyl Myristate | 8.02 |
| Castor Oil | 8.90 |
| Cholesterol | 9.55 |

As reported in *Solubility, Effects in Product, Package, Penetration and Preservation*, C. D. Vaughan, Cosmetics and Toiletries, Vol. 103, October 1988.

B) Rheology

The hydrophobic skin benefit agents for use in the benefit phase of the composition have a preferred rheology profile as defined by Consistency value (k) and Shear Index (n). Preferred Consistency value ranges are 1-10,000 poise $(1/sec)^{n-1}$, preferably 10-2000 poise $(1/sec)^{n-1}$ and more preferably 50-1000 poise $(1/sec)^{n-1}$. Shear Index ranges are 0.1-0.8, preferably 0.1-0.5 and more preferably 0.20-0.4.

The hydrophobic skin benefit agents can be characterized by Consistency value (k) and Shear Index (n) values as defined by the above-described ranges, wherein these defined ranges are selected to provide enhanced deposition and reduced stickiness during and after application of the personal cleaning composition on hair or skin.

The Shear index (n) and Consistency (k) values are well known and accepted industry standards for reporting the viscosity profile of materials having a viscosity that is a function of an applied shear rate.

The viscosity ($\mu$) for any material can be characterized by the relationship or equation $$[\mu = \sigma/\gamma']$$

wherein $\sigma$ is shear stress and $\gamma'$ is shear rate, so that the viscosity for any material can be measured by either applying a shear rate and measuring the resultant shear stress or vice versa.

The Carrimed CSL 100 Controlled Stress Rheometer is used to determine Shear Index, n, and Consistency value, k, for the hydrophobic skin benefit agents herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10-4 rad/sec, then this rate of strain is reported as a shear rate. These data are used to create a viscosity ($\mu$) versus shear rate ($\gamma'$) flow curve for the hydrophobic skin benefit agent material. This flow curve can then be modeled in order to provide a mathematical expression that describes the material's behavior within specific limits of shear stress and shear rate. These results are fitted with the following well-accepted power law model (see for instance: *Chemical Engineering*, by Coulson and Richardson, Pergamon, 1982 or *Transport Phenomena* by Bird, Stewart and Lightfoot, Wiley, 1960):

$$[\mu = k(\gamma')^{n-1}]$$

The Carrimed CSL 100 Controlled Stress Rheometer is used to perform oscillatory tests at 35° C. with the 4 cm 2° cone measuring system typically set with a 51 micron gap. The oscillatory tests at 35° C. are carried out in 2 steps. The first step is a stress amplitude sweep at the expected starting and ending frequencies for the frequency sweep. These tests allow a determination to be made as to whether or not the test conditions are within the linear viscoelastic region for the test material over the anticipated frequency range. The linear viscoelastic region is a region where there is a linear relationship between stress and strain. The second step is a frequency sweep made at a stress level within that linear viscoelastic region. The frequency sweep allows the test material's viscoelastic behavior to be measured. The oscillatory test on a controlled stress rheometer is performed by applying a stress in an oscillatory manner and measuring the resulting oscillatory strain response and the phase shift between the applied stress wave form and the resulting strain wave form in the test material. The resulting complex modulus is expressed as a combination of the material's elastic (G') and viscous (G") components. The elastic modulus G' is a measure of a materials ability to store recoverable energy. This energy storage can be the result of the ability of a complex polymer, structural network, or a combination of these to recover stored energy after a deformation. The viscous or loss modulus G" is a measure of the unrecoverable energy, which has been lost due to viscous flow.

The hydrophobic skin benefit agents suitable for use herein can include a variety of hydrocarbons, oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, polyglycerin fatty acid esters, lanolin and its derivatives, wax esters, beeswax derivatives, sterols and phospholipids, and combinations thereof.

Non-limiting examples of hydrocarbon oils and waxes suitable for use herein include petrolatum, mineral oil, micro-crystalline waxes, polyalkenes, paraffins, cerasin, ozokerite, polyethylene, perhydrosqualene, and combinations thereof.

Non-limiting examples of silicone oils suitable for use as hydrophobic skin benefit agents herein include dimethicone copolyol, dimethylpolysiloxane, diethylpolysiloxane, mixed C1-C30 alkyl polysiloxanes, phenyl dimethicone, dimethiconol, and combinations thereof. Preferred are non-volatile silicones selected from dimethicone, dimethiconol, mixed C1-C30 alkyl polysiloxane, and combinations thereof. Non-limiting examples of silicone oils useful herein are described in U.S. Pat. No. 5,011,681 (Ciotti et al.).

Non-limiting examples of diglycerides and triglycerides suitable for use as hydrophobic skin benefit agents herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof.

Non-limiting examples of acetoglyceride esters suitable for use as hydrophobic skin benefit agents herein include acetylated monoglycerides.

Non-limiting examples of alkyl esters suitable for use as hydrophobic skin benefit agents herein include isopropyl esters of fatty acids and long chain esters of long chain (i.e. $C_{10}$-$C_{24}$) fatty acids, e.g. cetyl ricinoleate, non-limiting examples of which include isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic skin benefit agents herein include oleyl myristate, oleyl stearate, oleyl oleate, and combinations thereof.

Non-limiting examples of polyglycerin fatty acid esters suitable for use as hydrophobic skin benefit agents herein include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hydrophobic skin benefit agents herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Still other suitable hydrophobic skin benefit agents include milk triglycerides (e.g., hydroxylated milk glyceride) and polyol fatty acid polyesters.

Still other suitable hydrophobic skin benefit agents include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

The benefit phase of the composition preferably comprises one or more hydrophobic skin benefit agents, wherein at least 20% by weight of the hydrophobic skin benefit agents are selected from petrolatum, mineral oil, sunflower seed oil, micro-crystalline waxes, paraffins, ozokerite, polyethylene, polybutene, polydecene and perhydrosqualene dimethicones, cyclomethicones, alkyl siloxanes, polymethylsiloxanes and methylphenylpolysiloxanes, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, castor oil, soy bean oil, maleated soy bean oil, safflower oil, cotton seed oil, corn oil, walnut oil, peanut oil, olive oil, cod liver oil, almond oil, avocado oil, palm oil and sesame oil, and combinations thereof. More preferably, at least about 50% by weight of the hydrophobic skin conditioning agents are selected from the groups of petrolatum, mineral oil, paraffins, polyethylene, polybutene, polydecene, dimethicones, alkyl siloxanes, cyclomethicones, lanolin, lanolin oil, lanolin wax. The remainder of the hydrophobic skin conditioning agent is preferably selected from: isopropyl palmitate, cetyl riconoleate, octyl isononanoate, octyl palmitate, isocetyl stearate, hydroxylated milk glyceride and combinations thereof.

Optional Ingredients

The separate benefit phase of the striped liquid personal cleansing compositions may optionally comprise the following skin benefit ingredients for enhanced delivery of these benefit materials on skin.

A) Desquamation Actives

Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett. Preferred concentrations of desquamation actives range from about 0.1% to about 10%, more preferably from about 0.2% to about 5%, even more preferably from about 0.5% to about 4%, by weight of the personal cleansing composition.

Another desquamation system that is suitable for use herein contains salicylic acid and zwitterionic surfactants and is described in U.S. Pat. No. 5,652,228 to Bissett. Zwitterionic surfactants such as described in these applications are also useful as desquamatory agents herein, with cetyl betaine being particularly preferred.

B) Anti-Wrinkle Actives/Anti-Atrophy Actives

Anti-wrinkle actives or anti-atrophy actives include sulfur-containing D and L amino acids and their derivatives and salts, particularly the N-acetyl derivatives. A preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, and skin peel agents (e.g., phenol and the like).

Hydroxy acids as skin active agents herein include salicylic acid and salicylic acid derivatives, preferred concentrations of anti-wrinkle/anti-atrophy actives range from about 0.01% to about 50%, more preferably from about 0.1% to about 10%, even more preferably from about 0.5% to about 2%, by weight of the personal cleansing composition.

Other non-limiting examples of suitable anti-wrinkle actives for use herein are described in U.S. Pat. No. 6,217,888, issued to Oblong et al.

C) Anti-Oxidants/Radical Scavengers

Non-limiting examples of anti-oxidants or radical scavengers for use herein include ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, butylated hydroxy benzoic acids and their salts, 6-hydroxy-2,5,7,8-tetramethylchroman-2-carboxylic acid (commercially available under the tradename Trolox®, gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used. The preferred concentrations range from about 0.1% to about 10%, more preferably from about 1% to about 5%, by weight of the personal cleansing composition.

D) Chelators

The term "chelating agent" or "chelator" refers to those skin active agents capable of removing a metal ion from a system by forming a complex so that the metal ion cannot readily participate in or catalyze chemical reactions.

The chelating agents as skin active agents for use herein are preferably included at concentrations ranging from about 0.1% to about 10%, more preferably from about 1% to about 5%, by weight of the personal cleansing composition. Non-limiting examples of suitable chelating agents are described in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995.

A preferred chelating agent for use in the compositions of the present invention includes disodium EDTA, and derivatives thereof.

E) Anti-Cellulite Agents

Non-limiting examples of anti-cellulite agents include xanthine compounds such as caffeine, theophylline, theobromine, aminophylline, and combinations thereof. Anti-cellulite agents are preferably included at concentrations ranging from about 0.1% to about 10%, more preferably from about 1% to about 5%, by weight of the personal cleansing composition.

F) Tanning Actives

Non-limiting examples of such tanning agents include dihydroxyacetone, which is also known as DHA or 1,3-dihydroxy-2-propanone. Tanning actives are preferably included at concentrations ranging from about 0.1% to about 10%, more preferably from about 1% to about 5%, by weight of the personal cleansing composition.

G) Skin Lightening Agents

Non-limiting examples of skin lightening agents suitable for use herein include kojic acid, arbutin, ascorbic acid and derivatives thereof (e.g., magnesium ascorbyl phosphate or sodium ascorbyl phosphate), and extracts (e.g., mulberry extract, placental extract). Non-limiting examples of skin lightening agents suitable for use herein also include those described in WO 95/34280, WO 95/07432, and WO 95/23780. Skin lightening agents are preferably included at concentrations ranging from about 0.1% to about 10%, more preferably from about 1% to about 5%, by weight of the personal cleansing composition.

H) Skin Soothing and Skin Healing Actives

Non-limiting examples of skin soothing or skin healing actives suitable for use herein include panthenoic acid derivatives (e.g., panthenol, dexpanthenol, ethyl panthenol), aloe vera, allantoin, bisabolol, and dipotassium glycyrrhizinate. Skin soothing and skin healing actives are preferably included at concentrations ranging from about 0.1% to about 10%, more preferably from about 1% to about 5%, by weight of the personal cleansing composition.

I) Antimicrobial Actives

Non-limiting examples of antimicrobial actives for use herein includes β-lactam drugs, quinolone drugs, ciprofloxacin, norfloxacin, tetracycline, erythromycin, amikacin, 2,4, 4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione, clotrimazole, and combinations thereof.

Antimicrobials are preferably included at concentrations ranging from about 0.1% to about 10%, more preferably from about 1% to about 5%, by weight of the personal cleansing composition.

J) Sunscreen Actives

Non-limiting examples of sunscreen actives, either organic or inorganic for use herein are described below. Among the inorganic sunscreens useful herein are metallic oxides such as titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof.

The concentration of the sunscreen active for use in the composition preferably ranges from about 0.1% to about 20%, more typically from about 0.5% to about 10%, by weight of the composition. Exact amounts of such sunscreen actives will vary depending upon the sunscreen or sunscreens chosen and the desired Sun Protection Factor (SPF).

A wide variety of conventional organic sunscreen actives are also suitable for use herein, non-limiting examples of which include p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane. Among these sunscreens, preferred are 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and combinations thereof.

K) Solid Particulates

Non-limiting examples of solid particulates for use herein include inorganic powders such as gums, chalk, Fuller's earth, talc, kaolin, iron oxide, mica, sericite, muscovite, phlogopite, synthetic mica, lepidolite, inorganic pigments, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), and boron nitride; organic powder such as polyamide resin powder (nylon powder), cyclodextrin, polyethylene powder, methyl polymethacrylate powder, polystyrene powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as titanium dioxide, zinc oxide, and magnesium oxide. Other solid particulates fore use herein are described in U.S. Pat. No. 5,688,831 (El-Nokaly et al.).

Preferred solid particulates for use herein are hydrophobically modified cornstarch (e.g., trade name Dry-Flo from National Starch) and particulate crosslinked hydrocarbyl-substituted polysiloxane (e.g., tradename Tospearl from GE Silicone). Mixtures of the above particulates may also be used.

Other suitable solid particulates for use herein include various moisture, sweat or sebum absorbing powders, non-limiting examples of which include silicas (or silicon dioxides), silicates, carbonates, various organic copolymers, and combinations thereof. The silicates are most typically those formed by the reaction of a carbonate or silicate with an alkali metal, alkaline earth metal, or transition metal, specific non-limiting examples of which include calcium silicate, amorphous silicas, calcium carbonate, magnesium carbonate, zinc carbonate, and combinations thereof. Non-limiting examples of some suitable silicates and carbonates for use herein are described in Van Nostrand Reinhold's *Encyclopedia of Chemistry*, 4$^{th}$ edition, pages 155, 169, 556, and 849 (1984). Absorbent powders are also described in U.S. Pat. No. 6,004,584 (Peterson et al.).

Other absorbent powders suitable for use herein include kaolin, mica, talc, starch, modified starch, microcrystalline cellulose (e.g., Avicel from FMC Corporation), or other silica-containing or non-silica-containing powder suitable for absorbing fluids from the applied surface of the body.

Solid particles are preferably included at concentrations ranging from about 0.1% to about 30%, more preferably from about 1% to about 5%, by weight of the personal cleansing composition.

L) Others

The personal cleansing compositions of the present invention may further comprise other optional ingredients that may modify the physical, chemical, cosmetic or aesthetic characteristics of the compositions or serve as additional "active" components when deposited on the skin. The compositions may also further comprise optional inert ingredients. Many such optional ingredients are known for use in personal care compositions, and may also be used in the personal cleansing compositions herein, provided that such optional materials are compatible with the essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. These optional materials can be used in any aspect of the compositions of the present invention, including either of the active or cleansing phases as described herein.

Optional ingredients for use in the cleansing phase of the compositions of the present invention can include any benefit phase material as described herein that is also compatible with the selected ingredients in the cleansing phase. Likewise, optional ingredients for use in the benefit phase of the compositions of the present invention can include any cleansing phase material described herein that is also compatible with the selected ingredients in the benefit phase.

Other optional ingredients for use in either phase of the composition, preferably the benefit phase, include silicone elastomer powders and fluids to provide any of a variety of product benefits, including improved product stability, application cosmetics, emolliency, conditioning, and so forth. The concentration of the silicone elastomers in the composition preferably ranges from about 0.1% to about 20%, more preferably from about 0.5% to about 10%, by weight of the composition. In this context, the weight percentages are based upon the weight of the silicone elastomers material itself, excluding any silicone-containing fluid that typically accompanies such silicone elastomers materials in the formulation process. The silicone elastomers suitable for optional use herein include emulsifying and non-emulsifying silicone elastomers, non-limiting examples of which are described in U.S. Ser. No. 09/613,266 (assigned to The Procter & Gamble Company).

Method of Use

The striped personal cleansing compositions of the present invention are preferably applied topically to the desired area of the skin or hair in an amount sufficient to provide effective delivery of the skin conditioning agent to the applied surface, or to otherwise provide effective skin conditioning benefits. The compositions can be applied directly to the skin or indirectly via the use of a cleansing puff, washcloth, sponge or other implement. The compositions are preferably diluted with water prior to, during, or after topical application, and then subsequently rinsed or wiped off of the applied surface, preferably rinsed off of the applied surface using water or a water-insoluble substrate in combination with water.

If the personal cleansing compositions contain stripes of varying colors it may be desirable to package these compositions in a transparent package such that the consumer can view the pattern through the package. Because of the viscosity of the subject compositions it may also be desirable to include instructions to the consumer to store the package upside down, on its cap to facilitate dispensing.

The present invention is therefore also directed to methods of cleansing the skin through the above-described application of the compositions of the present invention. The methods of the present invention are also directed to a method of providing effective delivery of the desired skin active agent, and the resulting benefits from such effective delivery as described herein, to the applied surface through the above-described application of the compositions of the present invention.

Method of Manufacture

The personal cleansing compositions of the present invention may be prepared by any known or otherwise effective technique, suitable for making and formulating the desired striped product form. It is especially effective to combine toothpaste-tube filling technology with a spinning stage design. Specific non-limiting examples of such methods as they are applied to specific embodiments of the present invention are described in the following examples.

Lather Volume

Lather volume of a striped liquid personal cleansing composition is measured using a graduated cylinder and a tumbling apparatus. A 1,000 ml graduated cylinder is chosen which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device which clamps the cylinder with an axis of rotation that transects the center of the graduated cylinder. One gram of the total personal cleansing composition (0.5 g of the cleansing phase and 0.5 g of the benefit phase) is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume. Compositions according to the present invention perform significantly better in this test than similar compositions in conventional emulsion form.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Each of the exemplified compositions provides improved deposition or effectiveness of the skin conditioning agents or optional ingredients delivered from each prepared composition.

Examples 1-3

The following examples described in Table 1 are non-limiting examples of cleansing phase and benefit phase compositions.

TABLE 1

Cleansing Phase and Benefit phase Compositions

| Ingredient | Example 1 wt % | Example 2 wt % | Example 3 Wt % |
|---|---|---|---|
| I. Cleansing Phase Composition | | | |
| Ammonium Laureth-3 Sulfate | 3.0 | 3.0 | 3.0 |
| Sodium Lauroamphoacetate (Miranol L-32 Ultra from Rhodia) | 16.7 | 16.7 | 16.7 |
| Ammonium Lauryl Sulfate | 1.0 | 1.0 | 1.0 |
| Lauric Acid | 0.9 | 0.9 | 0.9 |
| Trihydroxystearin (Thixcin R) | 2.0 | 2.0 | 2.0 |
| Guar Hydroxypropyltrimonium Chloride (N-Hance 3196 from Aqualon) | 0.17 | 0.75 | 0.75 |

TABLE 1-continued

Cleansing Phase and Benefit phase Compositions

| Ingredient | Example 1 wt % | Example 2 wt % | Example 3 Wt % |
|---|---|---|---|
| Guar Hydroxypropyltrimonium Chloride (Jaguar C-17 from Rhodia) | 0.58 | — | — |
| Polyquaterium 10 (UCARE polymer JR-30M from Amerchol) | 0.45 | — | — |
| Polymethacrylamidopropyltrimonium Chloride (Polycare 133 from Rhodia) | — | 0.24 | — |
| Polyquaternium-39 (Merqurt Plus 3300 from Calgon) | — | 0.81 | — |
| PEG 90M (Polyox WSR 301 from Union Carbide) | 0.25 | — | — |
| PEG-14M (Polyox WSR N-3000 H from Union Carbide) | 0.45 | 2.45 | 2.45 |
| Linoleamidoprypyl PG-Dimonium Chloride Phosphate Dimethicone (Monasil PLN from Uniqema) | — | 1.0 | 4.0 |
| Glycerin | 1.4 | 4.9 | 4.9 |
| Sodium Chloride | 0.3 | 0.3 | 0.3 |
| Sodium Benzoate | 0.25 | 0.25 | 0.25 |
| Disodium EDTA | 0.13 | 0.13 | 0.13 |
| Glydant | 0.37 | 0.37 | 0.37 |
| Citric Acid | 1.6 | 0.95 | 0.95 |
| Titanium Dioxide | 0.5 | 0.5 | 0.5 |
| Perfume | 0.5 | 0.5 | 0.5 |
| Water | Q.S. | Q.S. | Q.S. |
| II. Benefit phase Composition | | | |
| Petrolatum (SuperWhite Protopet from WITCO) | 75 | 45 | 40 |
| Mineral Oil (Kaydol White MO from WITCO) | 24.92 | 44.92 | 39.92 |
| Tospearl 2000 (from GE) | — | 10 | — |
| Dry-Flo AF (from National Starch) | — | — | 20 |
| Pigment | 0.08 | 0.08 | 0.08 |

The compositions described above are prepared by conventional formulation and mixing techniques. The cleansing composition 1 is prepared by first creating the following premixes: citric acid in water premix at 1:3 ratio, Guar polymer premix with Jaguar C-17 and N-Hance 3196 in water at 1:10 ratio, UCARE premix with JR-30M in water at about 1:30 ratio, and Polyox premix with PEG-90M and PEG-14M in Glycerin at about 1:2 ratio. Then, the following ingredients are added into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, UCARE premix, Polyox Premix, and the rest of water. Heat the vessel with agitation until it reaches 190° F. (88° C.). Let it mix for about 10 min. Cool the batch with a cold water bath with slow agitation until it reaches 110° F. (43° C.). Add the following ingredients: Glydant, perfume, Titanium Dioxide. Keep mixing until a homogeneous solution forms.

The cleansing composition 2 is prepared by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, the following ingredients are added into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Polycare 133, Merquat Plus 3300, Monosil PLN, and the rest of water. Heat the vessel with agitation until it reaches 190° F. (88° C.). Let it mix for about 10 min. Cool the batch with a cold water bath with slow agitation until it reaches 110° F. (43° C.). Add the following ingredients: Glydant, perfume, Titanium Dioxide. Keep mixing until a homogeneous solution forms.

The cleansing composition 3 is prepared by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, the following ingredients are added into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Monasil PLN, and the rest of water. Heat the vessel with agitation until it reaches 190° F. (88° C.). Let it mix for about 10 min. Cool the batch with a cold water bath with slow agitation until it reaches 110° F. (43° C.). Add the following ingredients: Glydant, perfume, Titanium Dioxide. Keep mixing until a homogeneous solution forms.

The benefit phase is prepared by adding petrolatum into a mixing vessel. Heat the vessel to 140° F. (60° C.). Then, add mineral oil, cosmetic pigment, and Dry-Flo AF or Tospearl with agitation. Let the vessel cool down with slow agitation.

The cleansing and benefit phases are packaged into a single container using conventional toothpaste-tube filler equipment. The sample stage spins the bottle during the filling process to create a striped appearance. The stripe size is about 6 mm in width and 100 mm in length. The products remain stable at ambient for at least 180 days.

Examples 4-6

The following examples described in Table 2 are non-limiting examples of cleansing phase and benefit phase compositions of the present invention.

TABLE 2

Cleansing Phase and Benefit phase Compositions

| Ingredient | Example 4 wt % | Example 5 wt % | Example 6 wt % |
|---|---|---|---|
| I. Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Polyquaterium 10 (UCare KG-30M) | 0.7 | — | — |
| Jaguar C-17 (from Rhodia) | — | 0.7 | — |
| Guar Hydroxypropyltrimonium Chloride (N-Hance 3196 from Aqualon) | — | — | 0.7 |
| PEG 90M (Polyox WSR 301 from Dow Chemical) | — | — | 0.2 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Water | Q.S. | Q.S. | Q.S. |
| (pH) | (6.0) | (6.0) | (6.0) |
| II. Benefit phase Composition | | | |
| Petrolatum (Superwhite Protopet from WITCO) | 75 | 75 | 75 |
| Mineral Oil (Hydrobrite 1000 PO from WITCO) | 24.92 | 24.92 | 24.92 |
| Colorona Magenta Cosmetic Pigment (from Rona) | 0.08 | 0.08 | 0.08 |

The compositions described above are prepared by conventional formulation and mixing techniques. The cleansing phase composition is prepared by first adding citric acid into water at 1:3 ratio to form a citric acid premix. The following ingredients are then added into the main mixing vessel in the following sequence: water, Miracare SLB-354, sodium chloride, sodium benzoate, Disodium EDTA, glydant. Start agitation of the main mixing vessel. In a separate mixing vessel, disperse polymers (Polyquaterium 10, Jaguar C-17, or N-Hance 3196) in water at 1:10 ratio and form a polymer premix. Add the completely dispersed polymer premix into the main mixing vessel with continuous agitation. Disperse Polyox WSR 301 in water and then add to the main mixing vessel. Then, add the rest of the water and perfume into the batch. Keep agitation until a homogenous solution forms.

The benefit phase is prepared by adding petrolatum into a mixing vessel. Heat the vessel to 140° F. (60° C.). Then, add Kaydol mineral oil and cosmetic pigment with agitation. Let the vessel cool down with slow agitation.

The cleansing and benefit phases are packaged into a single container using conventional toothpaste-tube filler equipment. The sample stage spins the bottle during filling process to create a striped appearance. The stripe size is about 6 mm in width and 100 mm in length. The products remain stable at ambient for at least 180 days.

Examples 7-9

The following examples described in Table 3 are non-limiting examples of cleansing phase and benefit phase compositions of the present invention.

TABLE 3

Cleansing Phase and Benefit phase Compositions

| Ingredient | Example 7 wt % | Example 8 wt % | Example 9 wt % |
|---|---|---|---|
| I. Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Water | Q.S. | Q.S. | Q.S. |
| (pH) | (6.0) | (6.0) | (6.0) |
| II. Benefit phase Composition | | | |
| Versagel M (Gelled Mineral Oil from Penreco) | 99.92 | — | — |
| Versagel ME (Gelled Hydrogenated Polyisobutene from Penreco) | — | 99.92 | — |
| Versagel MP (Gelled Isopropyl Palmitate from Penreco)) | — | — | 99.92 |
| Colorona Magenta Cosmetic Pigment (from Rona) | 0.08 | 0.08 | 0.08 |

The compositions described above are prepared by conventional formulation and mixing techniques. The cleansing phase composition is prepared by first adding citric acid into water at 1:3 ratio to form a citric acid premix. The following ingredients are then added into the main mixing vessel in the following sequence: water, Miracare SLB-354, sodium chloride, sodium benzoate, Disodium EDTA, glydant. Start agitation of the main mixing vessel. Then, add perfume into the batch. Keep agitation until a homogenous solution forms.

The benefit phase is prepared by adding Versagel into a mixing vessel. Heat the vessel to 190° F. Then, add cosmetic pigment with agitation. Let the vessel cool down with slow agitation.

The cleansing and benefit phases are packaged into a single container using conventional toothpaste-tube filler equipment. The sample stage spins the bottle during the filling process to create a striped appearance. The stripe size is about 6 mm in width and 100 mm in length.

All documents cited in the detailed description of the invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A striped personal cleansing article comprising a package containing a striped personal cleansing composition comprising:
    (a) a first stripe comprising a first cleansing phase comprising a surfactant and water; and
    (b) a second stripe comprising a first benefit phase comprising at least about 20%, by weight of said benefit phase, of a hydrophobic material having a solubility parameter of from about 5 to about 15 $(cal/cm^3)^{0.5}$; wherein the benefit phase has a Consistency value of from about 1 to about 10,000 poise;
    (c) a first additional stripe comprising the first cleansing phase; and
    (d) a second additional stripe comprising the first benefit phase;
    wherein said striped personal cleansing composition is in a form selected from the group consisting of liquid, semi-liquid, cream, lotion, gel, and mixtures thereof;
    wherein said stripes are separate and in physical contact within said package; and
    wherein the first benefit phase comprises zero percent by weight of the benefit phase of surfactant.

2. A personal cleansing article according to claim 1, wherein the hydrophobic material in the first benefit phase has a Vaughan Solubility Parameter of from about 5 to about 10 $(cal/cm^3)^{0.5}$.

3. A personal cleansing article according to claim 1, wherein the first benefit phase has a Shear Index of from about 0.1 to about 0.8.

4. A personal cleansing article according to claim 1, wherein the hydrophobic material represents at least about 50% by weight of the first benefit phase.

5. A personal cleansing article according to claim 1, wherein at least 20% by weight of the first benefit phase is selected from the group consisting of petrolatum, mineral oil, micro-crystalline waxes, paraffins, ozokerite, polyethylene, polybutene, polydecene, perhydrosqualene, dimethicones, cyclomethicones, alkyl siloxanes, polymethylsiloxanes, methylphenylpolysiloxanes, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, castor oil, soy bean oil, sunflower seed oil, maleated soy bean oil, safflower oil, cotton seed oil, corn oil, walnut oil, peanut oil, olive oil, cod liver oil, almond oil, avocado oil, palm oil, sesame oil, and combinations thereof.

6. A personal cleansing article according to claim 1, wherein the first cleansing phase comprises:
    (i) at least one anionic surfactant;
    (ii) at least one electrolyte; and
    (iii) at least one alkanolamide;

wherein the first cleansing phase is non-Newtonian shear thinning, and has a viscosity of equal to or greater than about 3000 centipoise.

7. A personal cleansing article according to claim 6, wherein the first cleansing phase comprises from about 3% to about 60%, by weight of said cleansing phase, of total active surfactant.

8. A personal cleansing article according to claim 6, wherein the electrolyte comprises an anion selected from the group consisting of phosphate, chloride, sulfate, citrate, and mixtures thereof; and a cation selected from the group consisting of sodium, ammonium, potassium, magnesium, and mixtures thereof.

9. A personal cleansing article according to claim 6, wherein the electrolyte is present at a level of from about 0.1% to about 15% by weight of the cleansing phase.

10. A personal cleansing article according to claim 1, wherein said personal cleansing composition further comprises a cationic deposition polymer.

11. A personal cleansing article according to claim 1, wherein said first cleansing phase comprises sodium trideceth sulfate.

12. A personal cleansing article according to claim 1, wherein said first cleansing phase comprises sodium lauroamphoactetate.

13. A personal cleansing article according to claim 1, wherein said hydrophobic material is petrolatum.

14. A personal cleansing article according to claim 1, wherein said hydrophobic material is mineral oil.

15. A personal cleansing article according to claim 1, wherein said first cleansing phase comprises:
   (i) at least one anionic surfactant;
   (ii) at least one electrolyte; and
   (iii) at least one amphoteric surfactant;

wherein the first cleansing phase is non-Newtonian shear thinning, and has a viscosity of equal to or greater than about 3000 centipoise.

16. A personal cleansing article according to claim 1, wherein said first cleansing phase further comprises a non-ionic surfactant.

17. A personal cleansing article according to claim 1, wherein said first benefit phase comprises petrolatum, mineral oil and a pigment.

18. A striped personal care product, comprising a personal care composition within a package, wherein the personal care composition comprises:
   a) a cleansing phase comprising an anionic surfactant, a zwitterionic surfactant, and a cationic polymer; and
   b) a benefit phase comprising from about 80% to about 99% of a hydrophobic benefit agent selected from the group consisting of petrolatum, mineral oil, and combinations thereof, wherein the benefit phase comprises zero percent by weight of the benefit phase of surfactant;

wherein the two phases are separate and in physical contact within the package in the form of a multitude of stripes.

19. The product of claim 18, wherein the anionic surfactant comprises ammonium laureth-3 sulfate, the zwitterionic surfactant comprises sodium lauroamphoacetate, and the cationic polymer comprises guar hydroxypropyltrimonium chloride.

20. The product of claim 19, wherein the hydrophobic benefit agent comprises petrolatum and mineral oil.

21. The personal care product of claim 20, wherein the benefit phase comprises zero percent by weight of the benefit phase of surfactant.

* * * * *